United States Patent
Ko et al.

(10) Patent No.: US 8,013,185 B2
(45) Date of Patent: Sep. 6, 2011

(54) METHOD FOR PREPARING UNSATURATED ALDEHYDE AND/OR UNSATURATED FATTY ACID USING FIXED-BED CATALYTIC PARTIAL OXIDATION REACTOR

(75) Inventors: Jun-Seok Ko, Daejeon Metropolitan (KR); Kyoung-Su Ha, Anyang-si (KR); Sung-Kyoo Park, Daejeon Metropolitan (KR); Sung-Soo Park, Seoul (KR); Se-Won Baek, Daejeon Metropolitan (KR); Dong-Hyun Woo, Daejeon Metropolitan (KR); Seong-Jin Kim, Daejeon Metropolitan (KR)

(73) Assignee: LG Chem, Ltd., Seoul (KR)

( * ) Notice: Subject to any disclaimer, the term of this patent is extended or adjusted under 35 U.S.C. 154(b) by 36 days.

(21) Appl. No.: 12/450,572

(22) PCT Filed: Apr. 3, 2008

(86) PCT No.: PCT/KR2008/001880
§ 371 (c)(1),
(2), (4) Date: Oct. 1, 2009

(87) PCT Pub. No.: WO2008/120956
PCT Pub. Date: Oct. 9, 2008

(65) Prior Publication Data
US 2010/0036157 A1 Feb. 11, 2010

(30) Foreign Application Priority Data
Apr. 3, 2007 (KR) .................. 10-2007-0032800

(51) Int. Cl.
*C07C 51/16* (2006.01)
(52) U.S. Cl. ........................ 562/547; 562/549
(58) Field of Classification Search .................. None
See application file for complete search history.

(56) References Cited

U.S. PATENT DOCUMENTS

| 4,203,906 A * | 5/1980 | Takada et al. ............... 549/248 |
| 6,069,271 A | 5/2000 | Tanimoto et al. |
| 6,808,689 B1 | 10/2004 | Matsumoto et al. |

FOREIGN PATENT DOCUMENTS

| EP | 1 471 046 | 10/2004 |
| JP | 11-130722 | 5/1999 |
| JP | 2001-137688 | 5/2001 |
| KR | 10-2000-0039469 | 7/2000 |
| KR | 10-0349602 | 8/2002 |
| KR | 10-2004-0005468 | 1/2004 |
| KR | 10-2005-0067069 | 6/2005 |
| KR | 10-2007-0093316 | 9/2007 |
| WO | WO 03/059857 | 7/2003 |
| WO | WO 2004/007064 | 1/2004 |
| WO | WO 2005/021149 | 3/2005 |
| WO | WO 2005/063674 | 7/2005 |

\* cited by examiner

*Primary Examiner* — Paul A Zucker
(74) *Attorney, Agent, or Firm* — McKenna Long & Aldridge LLP

(57) ABSTRACT

The present invention provides a method for preparing unsaturated aldehydes and/or unsaturated fatty acids from olefins using a fixed-bed catalytic partial oxidation reactor, in particular, a start-up method upon packing with catalysts and initiating the reaction, and a process for producing unsaturated aldehydes and/or unsaturated fatty acids with high yield.

8 Claims, 4 Drawing Sheets

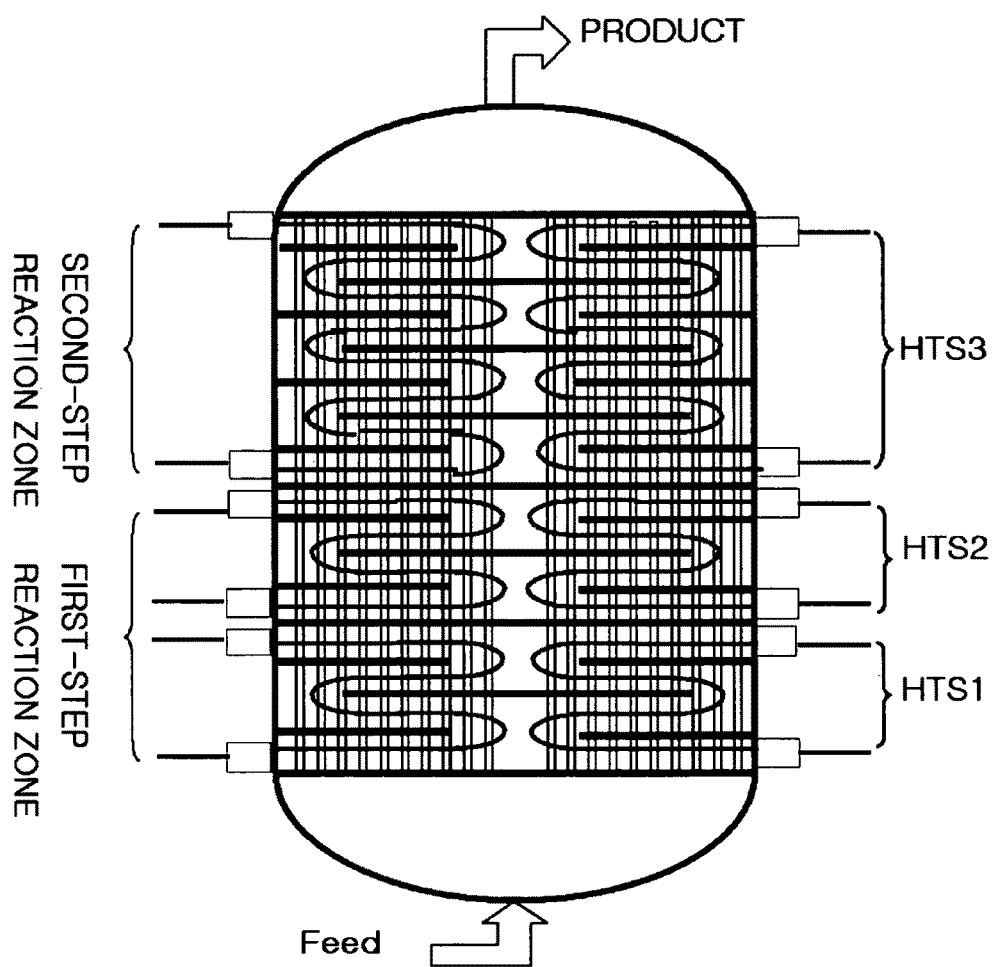
[Fig. 1]

[Fig. 2]
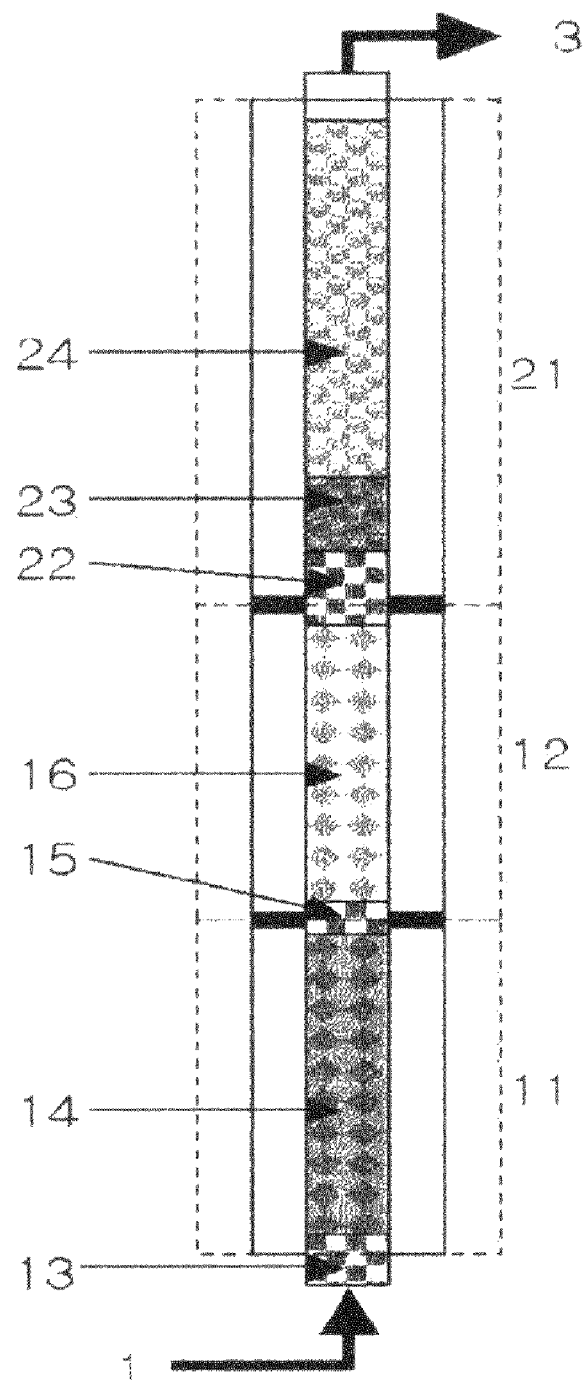

[Fig. 3]
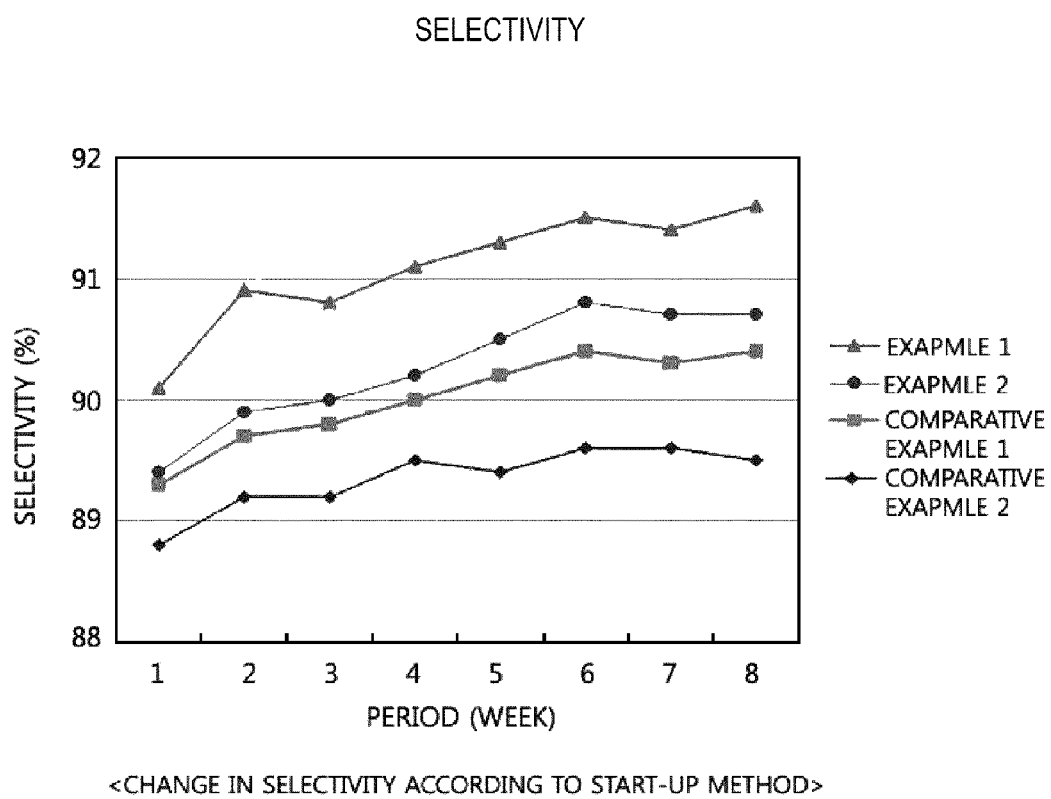
<CHANGE IN SELECTIVITY ACCORDING TO START-UP METHOD>

[Fig. 4]
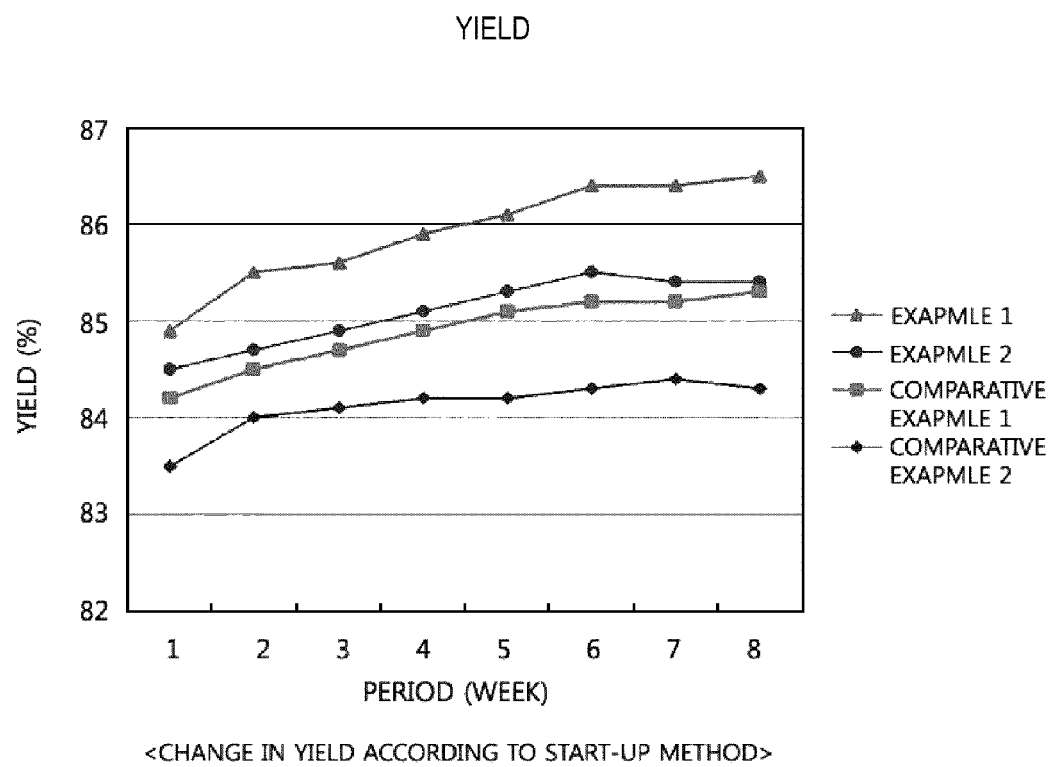
<CHANGE IN YIELD ACCORDING TO START-UP METHOD>

METHOD FOR PREPARING UNSATURATED ALDEHYDE AND/OR UNSATURATED FATTY ACID USING FIXED-BED CATALYTIC PARTIAL OXIDATION REACTOR

This application claims the benefit of PCT/KR2008/001880 filed on Apr. 3, 2008 and Korean Patent Application No. 10-2007-0032800 filed on Apr. 3, 2007, both of which are hereby incorporated herein by reference for all purposes in their entirety.

TECHNICAL FIELD

The present invention relates to a method for preparing unsaturated aldehydes and/or unsaturated fatty acids with high yield in a stable manner.

This application claims priority from Korea Patent Application No. 10-2007-0032800 filed on Apr. 3, 2007 in the KIPO, the disclosure of which is incorporated herein by reference in its entirety.

BACKGROUND ART

A process for producing unsaturated aldehydes and/or unsaturated acids from gas-phase olefins using a catalyst is a typical example of catalytic vapor phase oxidation. Typically, the catalytic vapor phase oxidation may be exemplified by a process for producing (meth)acrolein and/or (meth)acrylic acid by oxidizing propylene or propane, or a process for producing (meth)acrolein and/or (meth)acrylic acid by oxidizing isobutylene, t-butylalcohol or methyl-t-butylether.

To perform the catalytic vapor phase oxidation, solid-phase multi metal oxides are generally used as a catalyst. A composite oxide containing molybdenum and bismuth or molybdenum and vanadium, or a mixture thereof is generally used as a catalyst in the process for producing (meth)acrolein and/or (meth)acrylic acid. At least one type of catalyst in the form of granule is packed into a reaction tube, at least one reactant and air containing molecular oxygen as an oxidizing agent, molecular nitrogen as an inert gas, or raw material containing water vapor is in contact with the catalyst in the reaction tubes to perform vapor phase oxidation.

Generally, propane, propylene, isobutylene, t-butylalcohol or methyl-t-butylether is subjected to two-step catalytic vapor phase oxidation to form (meth)acrylic acid as a final product. More particularly, in the first-step reaction zone, propylene or the like is oxidized by oxygen, diluted inert gas, water vapor and an optional amount of catalyst to form (meth)acrolein as a main product. In the second-step reaction zone, (meth)acrolein obtained from the preceding step is oxidized by oxygen, diluted inert gas, water vapor and an optional amount of catalyst to form (meth)acrylic acid.

The catalyst used in the first-step reaction zone is an oxidation catalyst based on molybdenum-bismuth (Mo—Bi), which oxidizes propylene or the like to form (meth)acrolein as a main product. Additionally, a part of (meth)acrolein is further oxidized on the same catalyst to form (meth)acrylic acid partially. The catalyst used in the second-step reaction zone is an oxidation catalyst based on molybdenum-vanadium (Mo—V), which oxidizes (meth)acrolein-containing mixed gas produced in the first-step reaction zone, particularly (meth)acrolein, to form (meth)acrylic acid as a main product.

Since the catalytic vapor phase oxidation for producing (meth)acrolein and/or (meth)acrylic acid is performed at high temperature (200~600° C.) and is a highly exothermic reaction, heat transfer fluid such as molten salt is provided on the outer surface of reaction tubes to remove heat of reaction, whereby reaction temperature in the reaction tube is maintained at a predetermined temperature.

Reactors for carrying out the above process are realized in such a manner that each of the above two steps are implemented in one system or in two different systems. Further, the first-step reaction zone for producing (meth)acrolein by oxidizing propylene or the like may be divided into two or more reaction zones, as described in Korean Patent No. 10-0450234.

In the process for producing unsaturated aldehyde and/or unsaturated fatty acid from gas-phase propane, propylene, isobutylene, t-butylalcohol or methyl-t-butylether (referred to as 'propylene or the like' hereinafter), abnormal behaviors may occur at the initial start-up due to high reactivity of propylene or the like. Such abnormal behaviors deteriorating the catalyst include excessive rise of temperature of hot spots in catalyst layers due to explosive reaction according to material composition, excessive reaction due to high reaction temperature, or excessive rise of temperature of hot spots in catalyst layers, which is generated by high heat of reaction.

Further, in the case of producing (meth)acrolein and/or (meth)acrylic acid by feeding propylene or the like at a high space velocity and high concentration, the load of conversion in the catalyst layer is increased, resulting in excessive rise of temperature of hot spots in the catalyst layers. Therefore, heat accumulation occurs in the vicinities of the hot spots, which causes various problems such as loss of active ingredients from the catalyst layer and reduction in the number of active sites caused by the sintering of metal components, resulting in degradation in the quality of the catalyst layer.

DISCLOSURE OF INVENTION

Technical Problem

Accordingly, the present invention provides a method for preparing unsaturated aldehydes and/or unsaturated fatty acids from propylene or the like, which prevents the loss of catalytic activity due to excessive heat accumulation or hot spot formation in the catalyst layers, so as to increase the yield of the desired product.

Technical Solution

Accordingly, the present invention provides a method for preparing unsaturated aldehydes and/or unsaturated fatty acids from propylene or the like, in which the reaction zone for producing unsaturated aldehydes from propylene or the like is divided into two reaction zones forming sequentially the first and second reaction zones from the gas inlet, each reaction zone being packed with catalysts, and after reaction initiation, the temperature of hot spots in catalyst layers is controlled such a manner that the temperature of hot spots becomes higher in catalyst layer of the second reaction zone than in the first reaction zone at least during a start-up period.

Advantageous Effects

According to the present invention, the method for preparing unsaturated aldehydes and/or unsaturated fatty acids is performed to prevent excessive rise of temperature of hot spots in catalyst layers, which occurs at the initial start-up, and to produce aldehydes and/or unsaturated fatty acids with high yield in a stable manner.

BRIEF DESCRIPTION OF THE DRAWINGS

FIG. 1 is a schematic view showing the structure of a shell-and-tube heat exchanger reactor;

FIG. 2 is a schematic view showing the structure of a reaction tube packed with catalysts in the shell-and-tube reactor according to Examples and Comparative Examples;

FIG. 3 is a diagram showing the change in selectivity according to start-ups of Examples and Comparative Examples; and FIG. 4 is a diagram showing the change in yield according to start-ups of Examples and Comparative Examples.

BEST MODE FOR CARRYING OUT THE INVENTION

Hereinafter, the present invention will be described in detail as follows.

The present invention provides a method for preparing unsaturated aldehydes and/or unsaturated fatty acids from propylene or the like, in which the reaction zone for producing unsaturated aldehydes from propylene or the like is divided into two reaction zones forming sequentially the first and second reaction zones from the gas inlet, each reaction zone being packed with catalysts, and after reaction initiation, the temperature of hot spots in catalyst layers is controlled such a manner that the temperature of hot spots becomes higher in catalyst layer of the second reaction zone than in the first reaction zone during a start-up period, thereby preventing abnormal reaction at the initial start-up and deterioration of catalyst layers.

As used herein, the term "propylene or the like" refers to propane, propylene, isobutylene, t-butylalcohol, methyl-t-butylether or the like.

As used herein, the term "hot spot" refers to a peak temperature which is generated in a catalyst layer of the reaction tube in each reaction zone.

In the present invention, the reaction temperature in each reaction zone should be independently controlled.

In the method for preparing unsaturated aldehydes and/or unsaturated fatty acids according to the present invention, the temperature of hot spots in each reaction zone can be controlled by controlling the reaction temperature in each reaction zone.

Since the reaction temperature is determined by the temperature of heat transfer medium, which circulates the outer surface of reaction tube to absorb the heat of reaction generated in the reaction tube, it may correspond to the temperature of heat transfer medium.

Examples of the heat transfer medium include very highly viscous media, for example, molten salt. Examples of the molten salt may include a mixture of potassium nitrate and sodium nitrite, but are not limited thereto. Other examples of the heat transfer medium may include synthetic oil, diphenyl ether, polyphenyl, naphthalene derivatives and mercury.

In general, in the process for producing unsaturated aldehydes and/or unsaturated fatty acids, the reactor is divided into two reaction zones, including a reaction zone for producing unsaturated aldehydes by oxidizing propylene or the like and a reaction zone for producing unsaturated fatty acids by oxidizing the unsaturated aldehydes, whereby two-step oxidation is performed.

In the reaction zone for producing unsaturated aldehydes by oxidizing propylene or the like, a small amount of unsaturated fatty acid may be produced in addition to unsaturated aldehyde as a main product. For convenience, the reaction zone is described herein as a reaction zone for producing unsaturated aldehydes by oxidizing propylene or the like.

Meanwhile, the present invention is characterized in that the reaction zone for producing unsaturated aldehydes by oxidizing propylene or the like is divided into two reaction zones, forming sequentially the first and second reaction zones from the gas inlet, and the temperature of hot spots in the catalyst layer of each reaction zone is controlled.

After packing the reactor with catalysts and start-up, raw materials are fed into the inlet of reaction tube, and sequentially contact with each catalyst. Afterward, oxidation proceeds, resulting in conversion of propylene or the like into products such as unsaturated aldehyde and/or unsaturated fatty acid. Therefore, since the concentration of propylene or the like involved in the reaction is relatively high and the amount of oxygen is sufficient for the vigorous reaction in the inlet of reaction tube than other reaction zones, it is most important to control the reaction zone for producing unsaturated aldehydes from propylene or the like.

In particular, in the case where the reaction zone for producing unsaturated aldehydes by oxidizing propylene or the like is divided into two reaction zones, forming sequentially the first and second reaction zones from the inlet, the reaction temperature of first reaction zone is generally 5~20° C. lower than that of second reaction zone. However, in the case where the space velocity of propylene or the like is $100\,hr^{-1}$ or more, the temperature of hot spots in catalyst layers is higher in the first reaction zone than the second reaction zone. As described above, since the concentration of propylene or the like is higher in the first reaction zone than the second reaction zone, 50~80% propylene or the like of feed gas are converted into reactants even at a low reaction temperature to generate a large amount of heat, heat accumulation occurs to increase the temperature of hot spot, and the catalytic activity in the entire reaction tube may be partially deteriorated.

Since the reaction for producing unsaturated aldehydes by oxidizing propylene or the like is carried out in the first reaction zone by 50~80%, the concentration of feed gas such as propylene or the like is relatively low and the reaction is not rapidly carried out in the second reaction zone. Further, since the elevated temperature of hot spots in the catalyst layer does not readily decrease, it causes various problems such as sinter and loss of active ingredients from the catalyst layer, resulting in the loss of catalytic activity. The elevated temperature of hot spots in the catalyst layer does not readily decrease during the start-up period, which causes a decrease in the yield of products.

In order to solve the above problems, after the reactor is packed with catalysts, the temperature of hot spots is controlled such a manner that the temperature of hot spots becomes higher in the catalyst layer of the second reaction zone than that of the first reaction zone at the initial start-up.

During the start-up period and after completing the initial start-up, the difference in hot spot temperature between the first reaction zone and second reaction zone is preferably controlled within a range of 20° C.

Further, the process for producing unsaturated aldehyde and/or unsaturated fatty acid from propylene or the like of the present invention is preferably performed in a shell-and-tube heat exchanger reactor.

A schematic view of the shell-and-tube heat exchanger reactor is shown in the following FIG. 1. As shown in FIG. 1, the first-step reaction zone represents the reaction zone for producing unsaturated aldehydes by oxidizing propylene or the like, and the second-step reaction zone represents the reaction zone for producing unsaturated fatty acids by oxidizing unsaturated aldehyde. Further, the first-step reaction zone is divided into two reaction zones, where the temperature of heat transfer medium can be controlled, respectively.

The start-up period is generally within 30 days, preferably 3 to 10 days, and as used herein, the start-up period refers to a period when the space velocity of propylene or the like reaches 100 hr$^{-1}$ or more.

In order to solve various problems which may occur in the first reaction zone at the initial start-up, the method described in Korean Patent Application No. 10-2006-0023143 is performed as follows. After the reactor is packed with the catalysts, the method of the present invention is performed while the composition of feeding mixed gas and reaction temperature are gradually controlled for a predetermined period during start-up, thereby producing unsaturated aldehydes and/or unsaturated fatty acids with high yield in a stable manner. In addition, even though using propylene or the like at a high space velocity and high concentration, the process for producing unsaturated aldehydes and/or unsaturated fatty acids can be stably operated.

Further, it is preferable that unsaturated aldehyde and unsaturated fatty acid produced according to the present invention are (meth)acrolein and (meth)acrylic acid, respectively, but are not limited thereto.

MODE FOR THE INVENTION

Hereinafter, the preferred Examples are provided for better understanding. However, these Examples are for illustrative purpose only, and the invention is not intended to be limited by these Examples.

Example 1

As illustrated in FIG. 2, the following experiment was carried out in a pilot reactor, in which the first-step reaction zone for producing unsaturated aldehydes and the second-step reaction zone for producing unsaturated fatty acids were provided. The reaction tube had an inner diameter of 26 mm and a wall thickness of 2 mm. A heat transfer medium protection tube was installed in the reaction tube, and had an outer diameter of ⅛ inch, in which heat transfer medium was filled to measure the temperature of entire reactor. Reference numerals 11 and 12 denote the first-step reaction zone for producing unsaturated aldehydes. Reference numeral 11 denotes a first reaction zone, and HTS1 denotes molten salt circulating the outer wall of reaction tube in the first reaction zone. Reference numeral 12 denotes a second reaction zone, and HTS2 denotes molten salt circulating the outer wall of reaction tube in the second reaction zone. Reference numeral 21 denotes the second-step reaction zone for producing unsaturated fatty acids, and HTS3 denotes molten salt circulating the outer wall of reaction tube. The reactions zones 11, 12, and 21 were equipped to control the temperature of molten salts, independently. Raw materials were fed into the bottom 1 of the reactor, and products were discharged from the top 3 of the reactor. The reaction tube was packed with catalysts, sequentially 200 mm of inactive material layer 13, 1,550 mm of LGC1 14, 150 mm of inactive material layer 15, and 1,450 mm of LGC2 16 from the inlet. As a first-step catalyst material, the LGC1 and LGC2 were first-step oxidation catalyst layers based on molybdenum (Mo) and bismuth (Bi), and the preparation thereof is described in Korean Patent No. 0349602. Further, LGC1 and LGC2 had different catalytic activities, and the method of controlling the catalytic activities is described in Korean Patent Application No. 10-2005-0067069. Next to the LGC2 layer, 500 mm of mixed inactive material and 15% LGC4 were filled into 22. 800 mm of LGC3 were filled into 23, and 1,900 mm of LGC4 were filled into 25. The LGC3 and LGC4 were second-step catalyst materials, and the preparation thereof is described in Korean Patent No. 0378018 (Korean Patent Application No. 10-1998-0054814).

After the reactor was packed with the catalysts, a feed gas including 7.5 volume % of propylene, 13.8 volume % of oxygen, 7 volume % of water vapor and residual volume % of molecular nitrogen and inert gas was introduced during 7 days of start-up period, and then the final space velocity of propylene was 112.5 hr$^{-1}$. The temperature of hot spot and yield according to changes in the reaction temperature of the reactor for 8 wee ks are shown in Table 1, in which the yield of acrylic acid was 86.5% at 8 weeks after the start-up, the temperature of hot spot was allowed to be higher in the second reaction zone than in the first reaction zone until 5 weeks, and then difference in hot spot temperature between the first reaction zone and second reaction zone was within about 5° C. In the experiments described in the following Examples and Comparative Examples, the reaction temperature was controlled so that the conversion rate of propylene reached 97.5%~98.0% in the first step reaction zone for producing unsaturated aldehydes, and the temperature of HTS3 was controlled so that the volume of acrolein, not reacted in the outlet of the reactor, became 1.0~1.5 volume % in the second step reaction zone for producing unsaturated fatty acids.

The results are shown in the following Table 1.

TABLE 1

| Period (week) | 1 | 2 | 3 | 4 | 5 | 6 | 7 | 8 |
|---|---|---|---|---|---|---|---|---|
| HTS1 (° C.) | 295.0 | 296.0 | 296.0 | 297.0 | 297.0 | 298.0 | 298.0 | 299.0 |
| HTS2 (° C.) | 323.0 | 325.0 | 324.0 | 323.0 | 323.0 | 322.0 | 322.0 | 321.0 |
| Hot spot 1 (° C.) | 361.0 | 362.0 | 364.5 | 366.8 | 366.4 | 367.3 | 366.9 | 367.1 |
| Hot spot 2 (° C.) | 374.3 | 372.1 | 370.3 | 368.2 | 367.2 | 365.0 | 364.7 | 363.2 |
| Selectivity (%) | 89.8 | 90.9 | 90.8 | 91.1 | 91.3 | 91.5 | 91.4 | 91.6 |
| Yield (%) | 84.5 | 85.5 | 85.6 | 85.9 | 86.1 | 86.3 | 86.3 | 86.5 |

HTS: Heat Transfer Salt.
Hot spot 1: temperature of hot spot in first reaction zone
Hot spot 2: temperature of hot spot in second reaction zone
Conversion rate (%): [mole number of reacted propylene/mole number of supplied propylene] × 100
Selectivity (%): [(mole number of acrolein + mole number of acrylic acid)/mole number of supplied propylene] × 100
Yield (%): [mole number of acrylic acid/mole number of supplied propylene] × 100

Example 2

The experiment was performed in the same reactor as in Example 1, and the catalysts and the constitution of catalyst layers were the same as in Example 1. The start-up was performed for 24 hrs, and then the final space velocity of propylene was 112.5 hr$^{-1}$. The temperature of hot spot and yield according to changes in the reaction temperature of the reactor for 8 weeks are shown in Table 2, in which the yield of acrylic acid was 85.4% at 8 weeks after the start-up, the temperature of hot spot was allowed to be higher in the second reaction zone than in the first reaction zone until 5 weeks, and then difference in hot spot temperature between the first reaction zone and second reaction zone was within about 5° C.

The results are shown in the following Table 2.

TABLE 2

| Period (week) | 1 | 2 | 3 | 4 | 5 | 6 | 7 | 8 |
|---|---|---|---|---|---|---|---|---|
| HTS1 (° C.) | 293.0 | 294.0 | 294.0 | 295.0 | 295.0 | 296.0 | 296.0 | 297.0 |
| HTS2 (° C.) | 321.0 | 323.0 | 322.0 | 321.0 | 321.0 | 320.0 | 320.0 | 320.0 |
| Hot spot 1 (° C.) | 364.0 | 364.2 | 363.5 | 364.1 | 364.2 | 366.3 | 365.8 | 366.8 |

TABLE 2-continued

| Period (week) | 1 | 2 | 3 | 4 | 5 | 6 | 7 | 8 |
|---|---|---|---|---|---|---|---|---|
| Hot spot 2 (° C.) | 375.3 | 372.1 | 370.3 | 368.2 | 367.2 | 365.0 | 364.7 | 363.2 |
| Selectivity (%) | 89.4 | 89.9 | 90.0 | 90.2 | 90.5 | 90.8 | 90.7 | 90.7 |
| Yield (%) | 84.5 | 84.7 | 84.9 | 85.1 | 85.3 | 85.5 | 85.4 | 85.4 |

Comparative Example 1

The experiment was performed in the same reactor as in Example 1, and the catalysts and the constitution of catalyst layers were the same as in Example 1. The start-up was performed for 7 days, and then the final space velocity of propylene was 112.5 hr$^{-1}$. The temperature of hot spot and yield according to changes in the reaction temperature of the reactor for 8 weeks are shown in Table 4, in which the yield of acrylic acid was 85.3% at 8 weeks after the start-up, the temperature of hot spot was allowed to be 10~15° C. higher in the first reaction zone than in the second reaction zone after the start-up.

The results are shown in the following Table 3.

TABLE 3

| Period (week) | 1 | 2 | 3 | 4 | 5 | 6 | 7 | 8 |
|---|---|---|---|---|---|---|---|---|
| HTS1 (° C.) | 300.0 | 300.0 | 300.0 | 301.0 | 301.0 | 302.0 | 302.0 | 303.0 |
| HTS2 (° C.) | 315.0 | 315.0 | 315.0 | 317.0 | 317.0 | 319.0 | 320.0 | 320.0 |
| Hot spot 1 (° C.) | 368.3 | 368.1 | 367.8 | 368.5 | 368.3 | 368.5 | 369.2 | 369.8 |
| Hot spot 2 (° C.) | 357.1 | 356.9 | 356.8 | 358.4 | 358.2 | 359.2 | 359.6 | 359.4 |
| Selectivity (%) | 89.3 | 89.7 | 89.8 | 90.0 | 90.2 | 90.4 | 90.3 | 90.4 |
| Yield (%) | 84.2 | 84.5 | 84.7 | 84.9 | 85.1 | 85.2 | 85.2 | 85.3 |

Comparative Example 2

The experiment was performed in the same reactor as in Example 1, and the catalysts and the constitution of catalyst layers were the same as in Example 1. The start-up was performed for 24 hrs, and then the final space velocity of propylene was 112.5 hr$^{-1}$. The temperature of hot spot and yield according to changes in the reaction temperature of the reactor for 8 weeks are shown in Table 3, in which the yield of acrylic acid was 84.3% at 8 weeks after the start-up, the temperature of hot spot was allowed to be 10~15° C. higher in the first reaction zone than in the second reaction zone after the start-up.

The results are shown in the following Table 4.

TABLE 4

| Period (week) | 1 | 2 | 3 | 4 | 5 | 6 | 7 | 8 |
|---|---|---|---|---|---|---|---|---|
| HTS1 (° C.) | 300.0 | 300.0 | 300.0 | 301.0 | 301.0 | 302.0 | 302.0 | 303.0 |
| HTS2 (° C.) | 315.0 | 315.0 | 315.0 | 317.0 | 317.0 | 319.0 | 320.0 | 320.0 |
| Hot spot 1 (° C.) | 370.1 | 369.3 | 369.2 | 368.5 | 368.1 | 368.5 | 369.0 | 369.5 |
| Hot spot 2 (° C.) | 356.1 | 355.8 | 355.6 | 356.7 | 356.4 | 357.4 | 357.6 | 357.2 |
| Selectivity (%) | 88.8 | 89.2 | 89.2 | 89.5 | 89.4 | 89.6 | 89.6 | 89.5 |
| Yield (%) | 83.5 | 84.0 | 84.1 | 84.2 | 84.2 | 84.3 | 84.4 | 84.3 |

The results of Examples and Comparative Examples are summarized in FIGS. 3 and 4, which are graphs showing the changes in selectivity and yield according to the start-up method and hot spot control. As shown in drawings, when the flow rate of feed gas and temperature of hot spot were gradually controlled as in Example 1, the highest selectivity and yield were found.

The invention claimed is:

1. A method for preparing unsaturated aldehydes, unsaturated fatty acids, or unsaturated aldehydes and unsaturated fatty acids from propane, propylene, isobutylene, t-butylalcohol, or methyl-t-butylether by fixed-bed catalytic partial oxidation in a shell-and-tube heat exchanger reactor comprising a gas inlet and reaction tubes,
wherein a reaction zone for producing unsaturated aldehydes from propane, propylene, isobutylene, t-butylalcohol, or methyl-t-butylether is divided into two reaction zones fanning sequentially the first reaction zone for producing the unsaturated aldehydes and second reaction zones for producing the unsaturated fatty acids from the gas inlet, each reaction zone being packed with catalysts, and after reaction initiation, temperature of hot spots is controlled to be higher in a catalyst layer of the second reaction zone than in a catalyst layer of the first reaction zone at least during a start-up period.

2. The method according to claim 1, wherein the temperature of the hot spots in the catalyst layers is controlled using a heat transfer medium having a controlled temperature, circulating the outer surface of the reaction tubes.

3. The method according to claim 2, wherein the heat transfer medium is selected from the group consisting of molten salt, synthetic oil, diphenyl ether, polyphenyl, naphthalene derivatives and mercury.

4. The method according to claim 3, wherein the molten salt is a mixture of potassium nitrate and sodium nitrite.

5. The method according to claim 1, wherein the start-up period is within 30 days after reaction initiation.

6. The method according to claim 1, wherein the start-up period is a period when the space velocity of propane, propylene, isobutylene, t-butylalcohol, or methyl-t-butylether reaches 100 hr$^{-1}$ or more.

7. The method according to claim 1, wherein difference in the hot spot temperature of the catalyst layers between the first reaction zone and second reaction zone is within a range of 20° C.

8. The method according to claim 1, wherein the unsaturated aldehyde is (meth)acrolein and the unsaturated fatty acid is (meth)acrylic acid.

* * * * *